US010174280B2

(12) United States Patent
Corso et al.

(10) Patent No.: US 10,174,280 B2
(45) Date of Patent: Jan. 8, 2019

(54) APPARATUS, SYSTEM, AND METHOD PROVIDING FLUID FLOW FOR CELL GROWTH (71) Applicant: CorSolutions LLC, Groton, NY (US)

(72) Inventors: Thomas N. Corso, Groton, NY (US); Colleen K. Van Pelt, Groton, NY (US)

(73) Assignee: CorSolutions LLC, Groton, NY (US)

( * ) Notice: Subject to any disclaimer, the term of this patent is extended or adjusted under 35 U.S.C. 154(b) by 195 days.

(21) Appl. No.: 13/858,890

(22) Filed: Apr. 8, 2013

(65) Prior Publication Data

US 2013/0266929 A1    Oct. 10, 2013

Related U.S. Application Data (60) Provisional application No. 61/621,279, filed on Apr. 6, 2012.

(51) Int. Cl.
C12M 1/36 (2006.01)
C12M 1/21 (2006.01)
C12M 1/34 (2006.01)

(52) U.S. Cl.
CPC ............ *C12M 41/48* (2013.01); *C12M 41/00* (2013.01)

(58) Field of Classification Search
CPC ...... C12M 41/00; C12M 41/48; C12M 23/16; C12M 23/12; C12M 23/34; C12M 23/58; C12M 41/36; B01L 2400/0487; B01L 3/5027; B01L 2200/10; B01L 2300/0816; B01L 3/502738; B01L 3/50273; B01L 2300/0636; B01L 2300/0867; B01L 2300/0883; B01L 3/502746;
(Continued)

(56) References Cited

U.S. PATENT DOCUMENTS 4,100,801 A * 7/1978 LeMay ..................... G01F 5/00
                                                     73/202
4,894,342 A * 1/1990 Guinn et al. ............... 435/297.4
(Continued)

FOREIGN PATENT DOCUMENTS

WO    WO2009089512 A2    7/2009
WO    WO2011057380 A1    5/2011

OTHER PUBLICATIONS

De Mare et al., Feedback control of flow rate from a peristaltic pump using balance measurements, 2001, Proceedings of the European Control Conference, pp. 2164-2168.*

(Continued)

*Primary Examiner* — Sean E Conley
*Assistant Examiner* — Holly M Mull
(74) *Attorney, Agent, or Firm* — Bond, Schoeneck & King, PLLC; Joseph Noto (57) ABSTRACT An apparatus, system and method providing a fluid flow suitable to grow and maintain living cells in the fluid flow are disclosed. The apparatus includes a fluid displacement apparatus capable of providing at least one of positive and negative displacement of the fluid and configured to indirectly displace the fluid, an in-line flow sensor configured to directly measure the fluid flow, and a feed-back control in communication with the fluid displacement apparatus and the in-line flow sensor, wherein the feed-back control is configured to continuously control the fluid flow in response to the flow sensor measurements.

20 Claims, 6 Drawing Sheets (58) Field of Classification Search
CPC ......... B01L 2300/10; B01L 2400/0481; B01L
3/502715; B01L 2300/024; B01L
2300/0861; B01L 2300/087; B01L
3/5025; B01L 2300/0877; B01L
2300/0819; B01L 2200/143; B01L
2300/0864; B01L 2300/088; B01L 9/527;
B01L 3/5085; B01L 2200/027; B01L
2200/0621; B01L 2300/0829; B01L
2200/146; B01L 3/502; B01L 9/52; C12Q
2565/629; C12Q 1/689; B01J
2219/00743; B01J 2219/0097; B01J
2219/00986; G01N 15/1484; G01N
29/022; G01N 35/08; G01N 1/28; G01N
2035/00158
USPC ......... 435/286.5, 287.1, 287.2, 287.3, 288.5,
435/289.1, 297.1, 297.2, 303.1
See application file for complete search history.

(56) References Cited

U.S. PATENT DOCUMENTS

| | | | |
|---|---|---|---|
| 6,915,679 B2 | 7/2005 | Chien et al. | |
| 7,934,519 B2 | 5/2011 | Zantl | |
| 2001/0039045 A1* | 11/2001 | Chan | C12M 21/06 435/289.1 |
| 2002/0008032 A1 | 1/2002 | Hayenga | |
| 2002/0146817 A1* | 10/2002 | Cannon et al. | 435/289.1 |
| 2005/0089428 A1* | 4/2005 | Navarro | F16L 55/052 417/540 |
| 2005/0257595 A1* | 11/2005 | Lewis | G01F 25/0007 73/1.16 |
| 2006/0193730 A1 | 8/2006 | Rosenstein et al. | |
| 2006/0234372 A1* | 10/2006 | Donahue | C12M 35/04 435/293.1 |
| 2007/0243523 A1 | 10/2007 | Ionescu-Zanetti et al. | |
| 2007/0295082 A1* | 12/2007 | Kilian | G01F 1/6845 73/204.26 |
| 2008/0314450 A1* | 12/2008 | Hawker | A61L 2/18 137/2 |
| 2010/0009335 A1* | 1/2010 | Joseph et al. | 435/3 |
| 2011/0136179 A1 | 6/2011 | Bin/Le et al. | |

OTHER PUBLICATIONS

PCT International Search Report; PCT/US2013/035683 dated Jul. 29, 2013.

PCT Written Opinion of the International Searching Authority; PCT/US2013/035683 dated Jul. 29, 2013.

Supplementary European Search Report in corresponding application EP13773035, dated Oct. 14, 2015.

* cited by examiner

APPARATUS, SYSTEM, AND METHOD PROVIDING FLUID FLOW FOR CELL GROWTH

This application claims the benefit of the filing date of U.S. Provisional Patent Application No. 61/621,279, filed Apr. 6, 2012, which is hereby incorporated by reference in its entirety.

FIELD

The invention pertains to the field of fluidic displacement, and in particular precision fluid control applicable to microfluidics, including cell culture, 3D cell culture, lab-on-a-chip, body-on-a-chip, cells-on-chip, and the like.

BACKGROUND

Microfluidics deals with the behavior, precise control and manipulation of fluids that are geometrically constrained to a small, typically sub-millimeter scale. Typically, micro means one of the following features: small volumes (mL, µL, nL, pL, fL), small size, low energy consumption, and effects of the micro domain. Typically fluids are moved, mixed, separated or otherwise processed. Numerous applications employ passive fluid control techniques like capillary forces. In some applications external actuation means are additionally used for a directed transport of the media. Examples are rotary drives applying centrifugal forces for the fluid transport on the passive chips. Active micro-fluidics refers to the defined manipulation of the working fluid by active (micro) components as micro pumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reducing sample and reagent volumes. It is a multidisciplinary field intersecting engineering, physics, chemistry, microtechnology and biotechnology, with practical applications to the design of systems in which such small volumes of fluids will be used. Micro-fluidics emerged in the beginning of the 1980's and is used in the development of inkjet print-heads, DNA chips, lab-on-a-chip technology, micro-propulsion, and micro-thermal technologies. Advances in micro-fluidics technology are revolutionizing molecular biology procedures for enzymatic analysis (e.g., glucose and lactate assays), DNA analysis (e.g., polymerase chain reaction and high-throughput sequencing), and proteomics. The basic idea of micro-fluidic biochips is to integrate assay operations such as detection, as well as sample pre-treatment and sample preparation on one chip. An emerging application area for biochips is clinical pathology, especially the immediate point-of-care diagnosis of diseases. In addition, microfluidics-based devices, capable of continuous sampling and real-time testing of air/water samples for biochemical toxins and other dangerous pathogens are desired. Microfluidic technology is creating powerful tools for cell biologists to control the complete cellular environment, leading to new questions and new discoveries. Many diverse advantages of this technology for microbiology include: microenvironmental control ranging from mechanical environment to chemical environment, precise spatiotemporal concentration gradients, mechanical deformation, force measurements of adherent cells, confining cell, exerting a controlled force, fast and precise temperature control, electric field integration, cell culture, plant on a chip and plant tissue culture, and cells-on-a-chip, and body-on-chip, and tissue-on-a-chip.

A goal of modern biology is to understand the molecular mechanisms underlying cellular function. Recent developments combining microfabrication technology with cell culture techniques have produced many novel devices, providing an unprecedented ability to control the cellular environment. This emerging "cells-on-a-chip" in vitro technology has demonstrated great potential for offering faster, cheaper and more accurate prediction of a drug's in vivo pharmacokinetics and pharmacodynamics. As an example, rapid hepatocyte profiling has been demonstrated by several groups. As hepatoxicity is one of the primary causes of late drug withdrawal, having a more pertinent model for liver function would enable an increasingly accurate prediction of human response to drugs. In addition to the liver, cultured cells in microdevices have also been shown to mimic kidney function, lung function, the gastrointestinal tract, the vascular network, and tumor angiogenesis. Others have further extended this technology by creating devices that can reproduce multi-organ interactions. A single device is fabricated with multiple compartmentalized microenvironments. Each chamber has a different kind of cell cultured, representing an organ, and the chambers are connected with fluidic conduits. This technology has been coined "human-on-a-chip" or "body-on-a-chip".

In conventional assays, cells are cultured in a two-dimensional monolayer, immersed in excess medium. In contrast, cells in native tissue are surrounded by extracellular matrix and other supporting cells. This results in drastically different cell microenvironments between cell-based assays and in vivo tissue. This difference results in cell-based assays inadequately modeling the nutrient transport, shear stress, and both chemical and mechanical signaling processes of cells. The proof that improved models are needed is provided by the significant number of drugs that fail late in clinical trials. Consequently, the promising technology of merging cell culture with microfluidics is an exciting alternative because it offers unique advantages over conventional cell-based assays. Microfabrication allows for devices with precisely tailored geometries and flow patterns, resulting in controllable, reproducible and more in vivo-like microenvironments as researchers are able to control the transport of growth factors, reagents and oxygen inside the system. Cells cultivated in microdevices adhere to the walls or support, allowing the perfusion of medium inside the cell culture area. This both improves metabolic waste removal and continually renews nutrient supply, creating a more physiological-like situation. Furthermore, laminar flow in microfluidic systems enables the controlled application of shear stress. Microfluidic devices also allow for the generation of concentration gradients. A gradient can be produced by convergence of flow streams, where sequential segregation and re-addition of the streams produces a smooth gradient across a fluidic channel. This is an important advantage for the microfluidic approach because gradients play a role in a wide range of biological processes including development, inflammation, wound healing, and cancer metastasis. Finally, microfluidic approaches allow for three-dimensional cell culture to mimic the native tissue architecture. These advantages result in microfluidics offering improved correlation to in vivo results, as compared to classic cell culture.

In micro-fluidics, there is particular interest in channel diameters in the range of 10's of nanometers to 10's of millimeters. Since the flow rate of fluid in these systems can range from nanoliters per minute to 100's of microliters per minute, there is a need for precision flow control at low flow rates. The precise control of flow rates may be essential to the micro-device function. Uncontrolled variations in the flow rate and the fluid composition may produce a number of deleterious effects that compromise the utility and function of the device. Also, temporal variations in flow rate, such as pulsations, can produce variations in detector signal, reactions, and damage to materials or biological components in the device. The importance of flow control is even more critical for mixing of streams or creating gradients during the course of the experiment. Conventional pumping systems commonly used in microfluidics generally employ positive displacement methods, where the rate of mechanical displacement of a pump element, e.g., a lead-screw driven piston, peristaltic pump rollers, and syringe plunger movement, provides a proportional rate of liquid flow. This method scales down poorly to low flow rates and is unable to control fluid flow with sufficient accuracy. The origin of the low flow rate inaccuracies include: machining tolerances, bearings, quality, syringe inner diameter tolerances, seal component stiction, mechanical back lash, system back pressure on the delivery components, stepping motor noise, temperature changes, tubing fatigue, system backlash, check valve leakage, pump seal leakage, flexing and creep of mechanical seals, thermal expansion of components and compression of the working fluid. Many of these issues can produce errors in flow rate larger than the flow rates desired in micro-device experiments. Some systems rely on adding an air bubble (syringe), adding system back pressure, pulse dampeners and/or fluid volumes to dampen fluctuations when generating flow. These volumes produce relatively high hydraulic capacitance in the system. This capacitance, in conjunction with the high hydraulic resistance leads to slow time response. Many approaches have the disadvantage of running at a fixed rate and all of the above parameters result in a slow response because of system back pressure decreases (in conduction with the above parameters) catching up to the flow rate or displacement setting. Accordingly, there is a need in the art for a precision flow control system that is capable of delivering fluid at low flow rates in the range of about 1 nanoliter/minute to about 1 Liter/minute and varying the flow rate in a prescribed manner that is both predictable and reproducible as well as having a quick response for both an increase or decrease in flow rate, thus, allowing for biologically relevant fluidic waveforms in microfluidics.

SUMMARY

In accordance with one aspect of the present invention, there is provided a method for providing a fluid flow, including providing a fluid source in a fluidic system; providing a fluid displacement apparatus capable of providing at least one of positive and negative displacement of the fluid and configured to indirectly displace the fluid to establish a fluid flow within the system; providing an in-line flow sensor configured to directly measure the fluid flow; providing a feed-back control in communication with the apparatus and the in-line flow sensor, wherein the feed-back control is configured to continuously control the fluid flow in response to the flow sensor measurements; establishing a desired fluid flow through the fluidic system; exposing living cells to the fluid flow; and maintaining by operation of the feed-back control the desired fluid flow to a value suitable to grow and maintain the living cells in the fluid flow.

In accordance with another aspect of the present invention, there is provided a system for providing a fluid flow, including a fluidic system having a fluid source; a fluid displacement apparatus capable of providing at least one of positive and negative displacement of the fluid and configured to indirectly displace the fluid to establish a fluid flow within the system; an in-line flow sensor configured to directly measure the fluid flow; a feed-back control in communication with the apparatus and the in-line flow sensor, wherein the feed-back control is configured to continuously control the fluid flow in response to the flow sensor measurements to establish a fluid flow suitable to grow and maintain living cells in the fluid flow.

In accordance with another aspect of the present invention, there is provided an apparatus including a fluid displacement apparatus capable of providing at least one of positive and negative displacement of fluid disposed in a tube in contact with the fluid displacement apparatus and configured to indirectly displace the fluid in the tube to establish a fluid flow; an in-line flow sensor configured to directly measure the fluid flow created by operation of the fluid displacement apparatus; and a feed-back control in communication with the fluid displacement apparatus and the in-line flow sensor, wherein the feed-back control is configured to continuously control the operation of the fluid displacement apparatus in response to the flow sensor measurements to establish a fluid flow suitable to grow and maintain living cells in the fluid flow.

These and other aspects of the present invention will become apparent upon a review of the following detailed description and the claims appended thereto.

DETAILED DESCRIPTION

The present invention is directed to an apparatus, system and method for providing and maintaining a fluid flow suitable for cell growth. Preferably, the system includes a fluid path in which a desired fluid flow can be generated and maintained. More preferably, the fluid path is a loop. Preferably the fluid path includes flexible tubing. Preferably, the fluid path includes a conduit having a cross-sectional volume ranging from about 25 microns$^2$ to about 3.5 centimeters². More preferably, the fluid path has a circular cross-section having a circumference of from about 6 microns to about 2 centimeters.

A fluid path or fluid system is a path or system in which the fluid is separated from the ambient environment or exposed to a controlled environment. The nature of the path or system enables the fluid to be placed under pressure. The fluid is capable of access from outside the path or system by any number of manners, for example, the fluid flow can be accessed by a syringe inserted through a membrane which is in communication with the fluid path. Moreover, fluid may be added to the system by any number of manners, for example, by adding fluid to a closed reservoir or fluid source in communication with the fluid path or system. Likewise, fluid may be removed from the system by any number of manners, for example, by a collection vessel connected to the fluid path by a switching valve in a manner so as not to disrupt the fluid flow. The fluid can be recycled or disposed of. In an embodiment according to the present invention, the fluid is preferably cell culture media which can be contained in tubing, preventing contamination from the outside environment.

Fluid is indirectly displaced by an apparatus, when the fluid is displaced without the fluid directly contacting any of the moving parts of the apparatus, such as for example, a peristaltic pump acting upon a fluid filled tube. Conversely, fluid is directly displaced by an apparatus, when the fluid is displaced by directly contacting any of the moving parts of the apparatus, such as for example, the plunger of a syringe pump.

An active system is one in which an apparatus, such as a pump, actively displaces the fluid to create a flow, such as in a pressure-driven or pneumatic-driven flow system, as opposed to a passive system in which the fluid flow is driven by gravity.

The system in accordance with an embodiment of the present invention includes an apparatus configured to displace, preferably, indirectly displace, the fluid to establish a fluid flow within the fluid path. The fluid displacement apparatus is capable of providing positive and negative displacement of the fluid. The apparatus of the present invention includes pump mechanisms based on peristaltic, pneumatic (pressure displacement), hydraulic, piston, vacuum, centrifugal, syringe, and the like actions. Preferably, the apparatus is a pump, more preferably, the pump is a peristaltic pump. In a preferred embodiment, the apparatus is a peristaltic pump and the pump displaces fluid contained in flexible tubing to create a fluid stream.

In an embodiment of the present invention, living cells or tissue are exposed to the fluid system. Preferably, the living cells are introduced by a device disposed in the fluid path. Preferably, the living cells are introduced into an internal channel of the device. Preferably, the fluid is a growth medium suitable for growing and maintaining live cells or tissue. Suitable growth media having the required nutrients for culturing cells are known in the art. In an embodiment of the present invention, living cells or tissue are exposed to the fluid system. Preferably, the living cells are introduced by a device disposed in the fluid path. Preferably, the living cells are introduced into an internal channel of the device. Preferably, the fluid is a growth medium suitable for growing and maintaining live cells or tissue. Suitable growth media having the required nutrients for culturing cells are known in the art. Cells are grown and maintained at an appropriate temperature and gas mixture (typically, 37° C., 5% $CO_2$ for mammalian cells). Culture conditions vary widely for each cell type, and variation of conditions for a particular cell type can result in different phenotypes. Aside from temperature and gas mixture, the most commonly varied factor in culture systems is the cell growth medium. Recipes for growth media can vary in pH, glucose concentration, growth factors, and the presence of other nutrients. The growth factors used to supplement media are often derived from animal blood, such as calf serum. Also possible is the use of universal, fully defined and animal free alternatives like Serum-Free media. Common media types include balanced salt solutions, basal media, complex media, serum free media The system includes an inline flow sensor configured to directly measure the fluid flow as the fluid passes the sensor. The system includes a feedback control in communication with the fluid displacement apparatus and the inline flow sensor. The inline flow sensor measures the flow and communicates with a feedback control mechanism. Suitable types of flow sensor mechanisms include thermal pulse, ultrasonic wave, acoustic wave, mechanical, and the like. The inline sensor may be mechanical-based, electrically-based, motion-based, or MEMS-based. The sensor mechanism may be thermal, ultrasonic or acoustic, electromagnetic, or differential pressure in nature. One example of a sensor suitable for use in accordance with the present invention is a thermal-type flow sensor where the sensor typically has a substrate that includes a heating element and a proximate heat-receiving element or two. When two sensing elements are used, they are preferably positioned at upstream and downstream sides of the heating element relative to the direction of the fluid (liquid or gas) flow to be measured. When fluid flows along the substrate, it is heated by the heating element at the upstream side and the heat is then transferred non-symmetrically to the heat-receiving elements on either side of the heating element. Since the level of non-symmetry depends on the rate of fluid flow and that non-symmetry can be sensed electronically, such a flow sensor can be used to determine the rate and the cumulative amount of the fluid flow. This mechanism allows the flow to be measured in either direction. In one preferred embodiment, the temperature sensors and the heating element are in thermal contact with the exterior of the fluid transporting tube and as the fluid stream only contacts the internal surfaces of the tube, the fluid media avoids direct contact with the sensor and heating elements. This format type allows highly accurate and highly sensitive flow measurements to be performed.

Another example of a sensor suitable for use in accordance with the present invention includes Doppler ultrasonic flow meters operating on the Doppler effect, whereby the transmitted frequency is altered linearly by being reflected from particles and bubbles in the fluid. The net result is a frequency shift between transmitter and receiver frequencies that can be directly related to the flow rate. Another example of a sensor suitable for use in accordance with the present invention is a variation of the above, wherein a transit-time meter measures the difference in travel time between pulses transmitted in the direction of, and against, the flow.

The fluid displacement apparatus preferably includes a pump mechanical drive system, such as a motor, that is controlled by a motor drive control unit. When the desired set point is inputted to the feedback control system, the drive system is started and fluid is pumped. The inline sensor measures the flow rate and feeds a digital or analog signal to the feedback control system. The feedback control is configured to continuously control the fluid flow in response to the flow sensor measurements. The feedback control timing in accordance with the present invention is capable of a process signal speed of at least about one second, preferably at least about 40 milliseconds, and more preferably about 10 microseconds. The feedback control system subsequently processes the desired set point and the sensor feedback signal, determines any differences between the two values and sends further instructions or control signals to the pump drive system which in turn adjusts the flow rate, accordingly. This serves as a closed loop feedback system. The sensor may be located after the fluid displacement apparatus and may be located before or after the fluid accepting device.

In one embodiment, a proportional-integral-derivative controller (PID controller) is used as the feedback mechanism. The PID controller calculates any error differences between the flow sensor measured values and the desired set point, as well as any system disturbances. The controller then minimizes the error by adjusting the process control inputs to the drive motor.

The PID controller calculation (algorithm) may involve all three separate constant parameters (the proportional, the integral, derivative values) or use only one or two of the actions depending on the type of mechanical pump system and desired performance. These values can be interpreted in terms of time: P depends on the present error, I on the accumulation of past errors, and D is a prediction of future errors, based on current rate of change. When more than one parameter is used, the weighted sum of these three actions is used to adjust the fluid delivery via controlling and adjusting the fluid delivery rate. For a pneumatic or vacuum fluid displacement system, the control is for relative adjusting of the pressure regulation components that displace the liquid.

In an embodiment where the fluid displacement apparatus is a peristaltic pump, the feedback control mechanism communicates with the pump to adjust the fluid flow by changing the motor rotational speed relative to the feedback from the sensor. This allows for linear flow or waveform flow to be maintained via direct measurement feedback. In this manner, for example, a linear flow can be obtained via running the motor in a non-linear fashion. Typically, a peristaltic pump runs via constant velocity spinning rollers set for a given flow rate. In accordance with the invention, the fluid flow exiting the tubing being pinched by the rollers is measured and the feedback control adjusts the motor speed and direction to compensate or change the roller velocity to achieve or maintain the desired flow.

According to the invention, the fluid displacement apparatus, inline flow sensor, and feed-back control are configured to maintain the fluid flow to a value suitable to grow and maintain living tissue or cells in the fluid stream. Shear stress is a flow-induced force exerted on the wall of the flow tube. This force relies upon units of force per unit square area. The flow rate can be calculated from the following relationship: $Q=\tau A/6\mu$, where Q is the fluid flow rate ($m^3$/sec), T is the shear stress ($N/m^2$), $\mu$ is the fluid viscosity ($Nm/s^2$), and A is related to the geometry of the tube or structure.

The magnitude of the fluid flow rate is linearly dependent on the shear stress. Since the fluid viscosity and density are temperature dependent, changes in temperature affect the shear stress, hence the flow rate measurement. The effect of temperature on density is usually small, and when temperature increases, the fluid viscosity usually increases, so the shear force usually decreases.

The system is configured to establish and maintain a fluid flow having a shear stress value in the fluid path of between about 0.01 dynes/$cm^2$ and about 60 dynes/$cm^2$, preferably, between about 0.1 dynes/$cm^2$ and about 50 dynes/$cm^2$, more preferably, between about 0.4 dynes/$cm^2$ and about 40 dynes/$cm^2$, by operation of the feedback control for longer than about 12 hours, preferably longer than about 24 hours, more preferably longer than about 48 hours, and most preferably for longer than 1 or 2 days. The fluid displacement apparatus can run for weeks at a time and is designed to run indefinitely, barring mechanical breakdown.

The system is configured to achieve a fluid flow rate in the range of from about 2 nanoliters/min. to about 1 Liter/min, preferably from about 1 milliliter/min to about 20 millilitesr/min, more preferably from about 1 microliters/min. to about 10 milliliters/min., and most preferably from about 1 microliter/min. to about 1 milliliter/min.

The system is configured to maintain the fluid flow at a constant velocity with pulsing less than from about 0.01% to about 20%, preferably less than about 5%, more preferably less than about 1%, of the set point.

The system is configured to maintain the fluid flow rate by changing the velocity at a rate of from about 0.01 to about 10 dynes per millisecond. The system is configured to be able to change shear set points by changing the fluid velocity at a rate of 1 dyne/$cm^2$ per second, preferably 1 dynes/$cm^2$ per 100 milliseconds, and more preferably 10 dynes/$cm^2$ per millisecond. The system is configured to change flow rate set points at rates of 1 mL per second, preferably 1 mL per 100 milliseconds, and more preferably 1 mL per millisecond.

The system is configured to provide a fluid flow profile ranging from about 0.2 Hz to about 20 Hz.

Preferably, the system further includes a fluid collection vessel in the fluid path configured to collect a sample of the fluid, for example, by a switch valve, wherein the pump can compensate and adjust fluid rate to match the removal rate without disrupting the fluid flow rate.

Preferably, the system further includes a heating or cooling element configured to adjust the temperature of the fluid.

Preferably, the system further includes a bubble trap configured to remove or trap bubbles in a specific location from the fluid without disrupting the fluid flow rate or allowing the bubbles to travel past the trap. The bubble trap is configured to avoid the need for degassing the vacuum, which could otherwise change the properties of the fluid. Bubbles are notorious in microfluidics for compromising experimentation. The present invention in a preferred embodiment implements a flow path with geometry to specifically trap bubbles via a change in path, shape or edge. In one embodiment, a tubing dampener has a single or double apical geometry. Also a change in edge profile, or topography may be implemented to keep bubble(s) from continuing on while allowing fluid to continue moving forward. Bubbles passing through the pump, reliably and reproducibly can become trapped in one of two apex regions of the dampener. The geometry of this dampener has been designed to also serve as a bubble trap. To void the pump of the collected bubbles, a volume of air is preferably swept through the dampener region. Other ways for purging out the bubble include a high velocity passage of liquid or a liquid with different wetting or surface tension properties. Depending on the volume of bubbles collected, this air sweep would most likely be performed only once every week or several months, according to usage.

In accordance with another embodiment, the present invention is directed to a method for providing a fluid flow, including providing a fluid source in a fluidic system; providing an apparatus configured to displace, preferably indirectly displace, the fluid to establish a fluid flow within the system; providing an in-line flow sensor configured to directly measure the fluid flow; providing a feed-back control in communication with the apparatus and the in-line flow sensor, wherein the feed-back control is configured to continuously control the fluid flow in response to the flow sensor measurements; establishing a fluid flow through the fluidic system; and exposing living cells to the fluid flow, wherein the fluid flow is maintained by operation of the feed-back control to a value suitable to grow and maintain living cells in the fluid. Preferably, the fluid flow is maintained to a shear stress value between about 0.01 dynes/cm$^2$ and about 60 dynes/cm$^2$; and more preferably to a value between about 0.1 dynes/cm$^2$ and about 40 dynes/cm$^2$. Preferably, the system is capable of maintaining the fluid flow for longer than about 12 hours, more preferably 24 hours, even more preferably 3 days, and most preferably more than one week.

Figure 1:
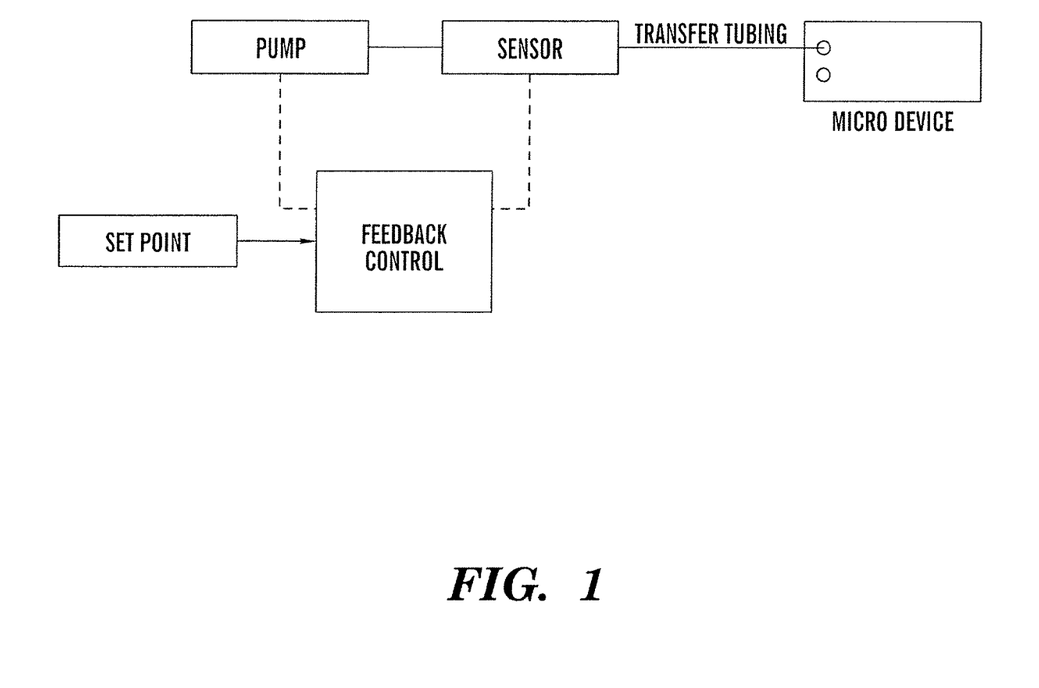
FIG. 1 is a schematic of the apparatus in accordance with an embodiment of the present invention.

FIG. 1 shows a pressure driven flow system with an in-line sensor for measuring the delivered flow rate and a mechanism feedback system for closed loop control. The flow is directly measured by the flow sensor. The flow sensor is in communication with the feedback control and may be located between the flow delivery apparatus and upstream of the micro-device, as shown in FIG. 1, or between the flow delivery apparatus and downstream from the micro-device. The desired set point is inputted to the feedback control system and the inline sensor measures the flow rate and feeds a digital or analog signal to the feedback control system. The feedback control system subsequently processes the desired set point and the sensor feedback signal, determines any differences between the two values and sends further instructions or control signals to the pump drive system which in turn adjusts the flow rate, accordingly. The sensor may be located after the fluid displacement apparatus and may be located before or after the fluid accepting device.

Feedback control between the sensor and the flow delivery system allows for direct control over the flow delivery system and the ability to change the output fluid velocity of the pump in a controlled fashion. The sensor and feedback allows for the flow delivery system to change parameters or changes in the moving parts in order to provide a constant fluid velocity allowing for smooth flow with pulsing less than 1% of the set point. The flow rates of the fluid delivery system and sensor may range from about 2 nL/min to 1 Liter/min in order to generate shear stresses in the range of about 0.01 to 60 dynes/cm$^2$. Additionally, the flow sensor adds the ability to log the actual flow rate and record the information to a data system as opposed to fluid delivery systems that have no direct fluidic measuring capability.

Figure 2:
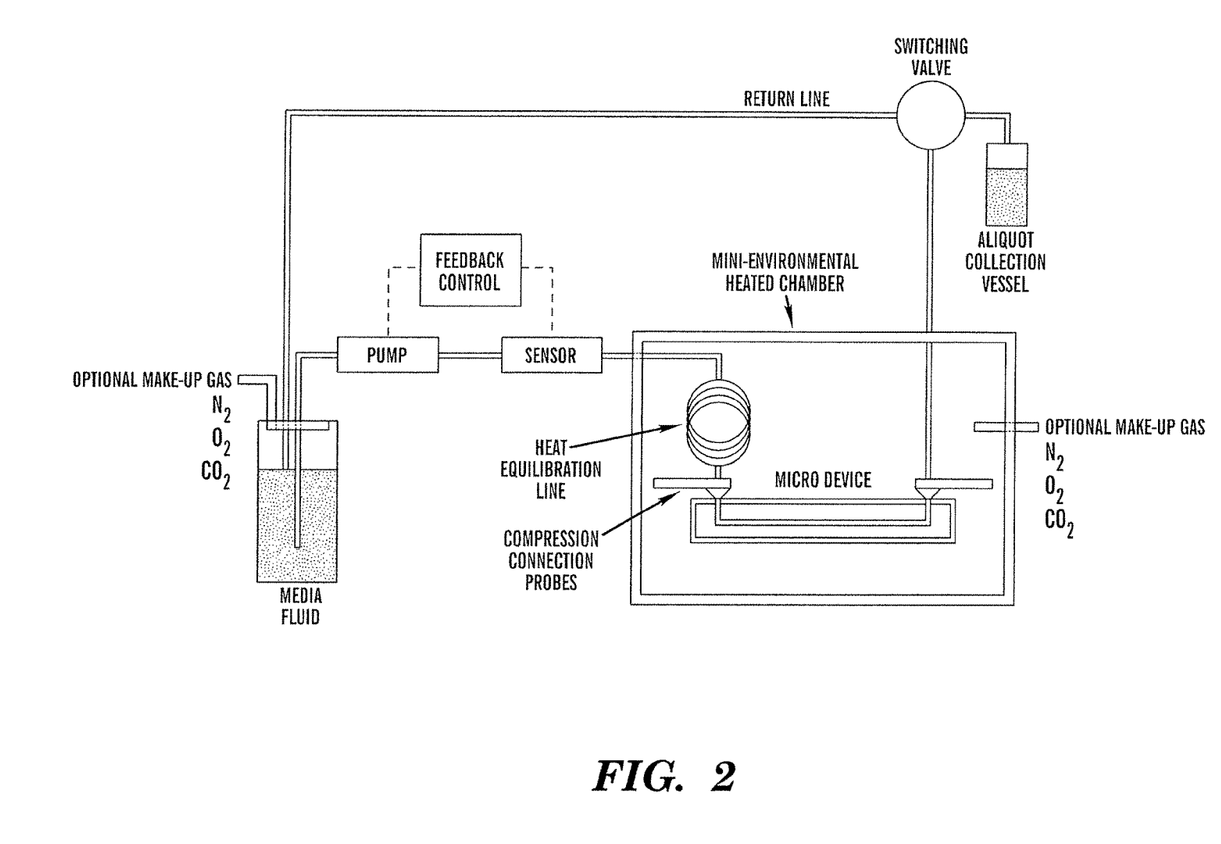
FIG. 2 is a schematic of the system in accordance with an embodiment of the present invention.

FIG. 2 shows a schematic diagram of a system for providing fluid flow in accordance with the present invention. When a peristaltic pump is activated, fluid travels through a tube from a container through pump tubing where a series of spaced apart pump rollers configured on a rotating member pinch the tubing to displace the fluid in a flow direction. The fluid flows through an in-line flow sensor where the flow of the fluid is directly measured. As shown in FIG. 1, the measurement signal from the flow sensor is sent to the feedback control and the feedback control sends a signal to the pump motor in response to the flow measurement to adjust the speed and direction of the rotating member to achieve or maintain the set flow value, as needed. The temperature of the fluid can be adjusted through the optional heating or cooling system, if desired, prior to entering the micro-device. Fluid exits the micro-device through a tube to the optional switching valve shown in FIG. 2, where the fluid can be optionally sampled in the aliquot collection vessel. Optionally, the un-sampled fluid returns to the fluid reservoir through the return line for reuse.

Figure 4:
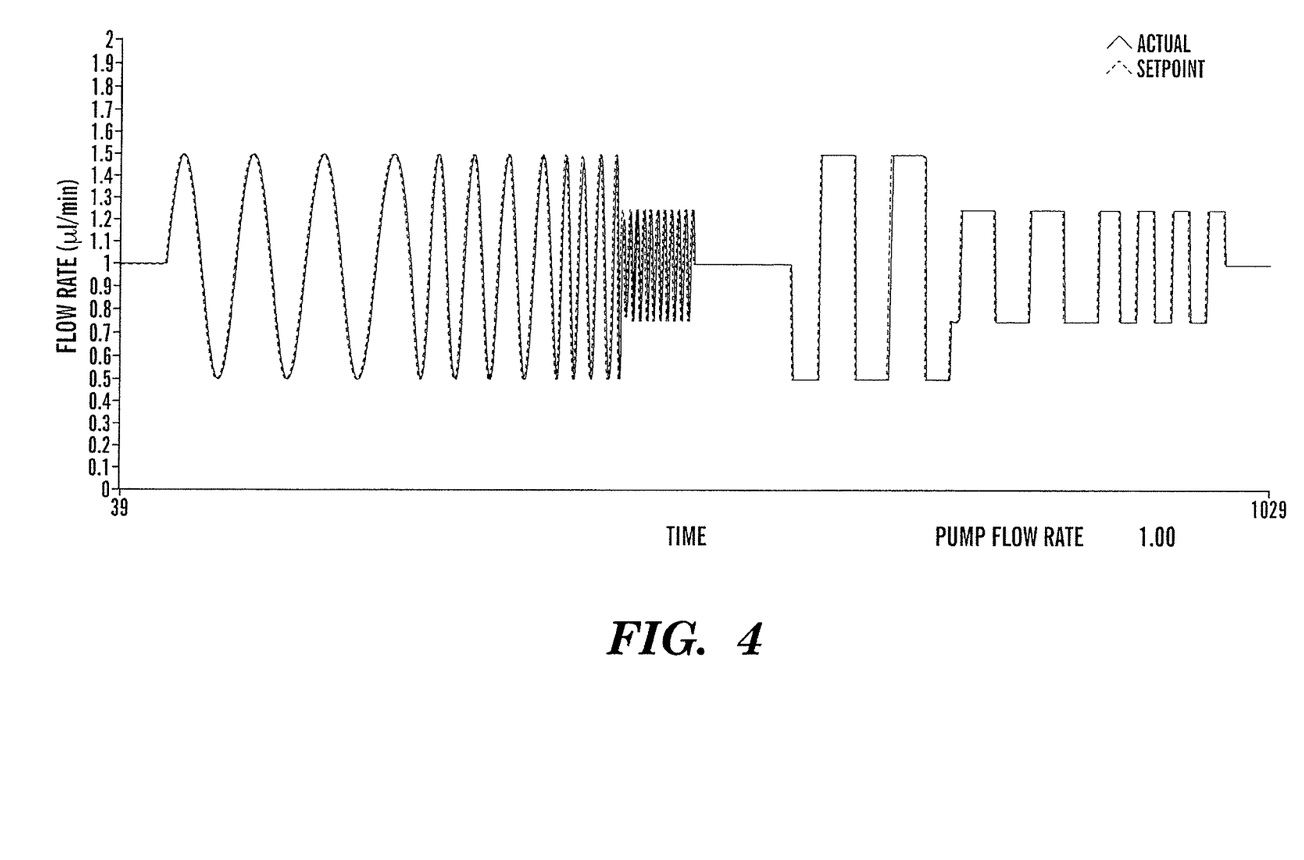
FIG. 4 is a graph of the flow rate vs. time generated by an apparatus in accordance with an embodiment of the present invention.

In addition to providing stable pulse flow at less 20% to 0.01% from the set point, the flow sensor allows for varying fluidic profiles such as sine waves and square waves, as shown in FIG. 4. A variety of other profiles include, for example, triangular, non-symmetrical or that of a biological profile such as a heart from a living system. In accordance with the present invention, a rate of change of 10 dyne per 1 millisecond is preferred. Preferably, the rate of change of flow velocity is from 0.01 to 10 dyne per 1 millisecond. A fast rate of change may be desired for studies around simulated Arrhythmia or palpitations research. Optionally, a restrictor or pulse dampener may be placed after the flow delivery system, before or after the fluidic device in order to generate high system backpressure or change the system elasticity relative to the delivered flow.

Flow through a blood vessel is determined by two factors: (1) the force that pushes the blood through the vessel, and (2) the resistance of the vessel to the blood flow. Ordinarily, the rate of blood flow is measured in milliliters or liters per minute (ml/min or l/min). The blood flow in the entire human circulation is about 5000 ml/min at rest in an average sized adult, but may be 5-6 times as great during heavy exercise when the body needs more oxygen to fuel that exercise. The amount of blood pumped by the heart in one minute is called the cardiac output. These numbers may be higher or lower for other animal types.

Since capillaries, arteries, and veins are elastic in nature their relative size changes in response to pressure and flow changes. Often micro-devices are more rigid or less elastic and the ability of the present invention to change flow rapidly enables the in vitro devices to more accurately simulate in vivo conditions. In an embodiment, the system contains a microfluidic pump having closed loop feedback to the pump delivery mechanism based on direct flow measurement for application in microfluidics in general. This allows for removing the pulsing of the fluid flow, even at very low flow rates. Further, fluidic waveforms can be created based on the flow. The pump can reverse direction quickly to make flow changes allowing the system to respond to changes, for example, in system back pressures, and environmental temperature changes that would affect thermal expansion of the tubing.

Feedback flow control according to the present invention allows for the convergence of cell culture and microfluidics for providing more accurate in vitro models for metabolism, toxicity, drug development, and biomedical studies. Changing the motor rotational speed relative to the feedback from the sensor allows for linear flow or waveforms to be maintained via direct measurement feedback. This enables pump profiles to mimic biological systems. Moreover, as tube fatigues occur in peristaltic based designs the direct flow feedback compensates for any offset required to maintain the desired flow.

In accordance with one embodiment, the direct flow measurement controls the pumping source (software or embedded electronics) for creating varying flow rate profiles for applications in body-on-a-chip. Varying flow profiles may be created for testing such parameters as shear forces, biological adhesion, nutrient up take, and pressure effects.

The merger of cell culture and microfluidics has created an area that has been coined "cells-on-a-chip" or "body-on-a-chip". This nascent, in vitro application area offers the potential for more accurate modeling of in vivo results as compared to classical cell culture. This is because the approach offers many benefits over conventional cell culture, and specifically the micrometer dimensions in the microfluidic devices allow for a high surface area to volume ratio, leading to more effective nutrient transfer, and allowing a more in vivo-like cellular environment in terms of cell secretion and signaling. Furthermore, there is no turbulence in the microchannels as fluid flow is laminar, allowing mass transport to be through diffusion, similar to a cell's natural environment. Consequently, microfluidic approaches allow for biomolecular gradients to be imitated. Additionally microfluidic devices allow for 3D cell culture, as compared to the just 2D permitted by classical cell culture.

The present invention provides a platform to interconnect microfluidic, "cells-on-a-chip" devices with pumps and detectors of the macro-world. The system offers reliability, compatibility with all substrate materials, ease-of-use with little training, flexibility for use with chips having varied architectures, chemical compatibility, allowance of maximum field of view for optical assessment, remain leak-free over a wide-range of flow rates and backpressures, be low in cost, and have potential for automation.

The present approach integrates leak-tight compression connections, and active flow control peristaltic fluid delivery pumps into a platform system. The platform differs from the conventional, cumbersome incubator, and offers an alternative of heated inserts with recessed areas to accept the microfluidic devices. Cell culture media can be maintained in bottles, wherein the headspace can be supplied with the desired concentrations of $CO_2$ and $O_2$, and this closed-loop platform approach eliminates the need to control humidity. Therefore the approach also offers a method of environmental control, addressing the incompatibility issues of microfluidic culture with conventional incubators. Thus, this user-friendly platform offers an innovative interface solution for "cells-on-a-chip" applications. The system with its built in pumps and environmental control serves as a "cardiovascular system" as it controls the metabolic and physical state of the tissue.

The present invention provides a commercially viable solution to the problem of interfacing microfluidics with the macro-world and allow for "cells-on-a-chip" and other microfluidic applications to become an integral part of biological and hospital laboratories, enabling scientific discoveries and greater understanding of complex biological systems.

In conventional assays, cells are cultured in a two-dimensional monolayer, immersed in excess medium. In contrast, cells in native tissue are surrounded by an extracellular matrix and other supporting cells. This results in drastically different cell microenvironments between cell-based assays and in vivo tissue. This difference results in cell-based assays inadequately modeling the nutrient transport, shear stress, and both chemical and mechanical signaling processes of cells. The proof that improved models are needed is provided by the significant number of drugs that fail late in clinical trials. Consequently, the technology of the present invention merging cell culture with microfluidics is a viable alternative because it offers unique advantages over conventional cell-based assays. Microfabrication allows for devices with precisely tailored geometries and flow patterns, resulting in controllable, reproducible and more in vivo-like microenvironments as researchers are able to control the transport of growth factors, reagents and oxygen inside the system. Cells cultivated in microdevices adhere to the walls, allowing the perfusion of medium inside the cell culture area. This both improves metabolic waste removal and continually renews nutrient supply, creating a more physiological-like situation. Furthermore, laminar flow in microfluidic systems enables the controlled application of shear stress. Microfluidic devices also allow for the generation of concentration gradients. A gradient can be produced by convergence of flow streams, where sequential segregation and re-addition of the streams produces a smooth gradient across a fluidic channel. This is an important advantage for the microfluidic approach of the present invention because gradients play a role in a wide range of biological processes including development, inflammation, wound healing, and cancer metastasis. Finally, microfluidic approaches allow for three-dimensional cell culture to mimic the native tissue architecture. These advantages provided by the present invention result in microfluidics offering improved correlation to in vivo results, as compared to classic cell culture.

The convergence of cell culture and microfluidics shows great promise for providing more accurate in vitro models for metabolism, toxicity, drug development, and biomedical studies. The present invention proposes to fill this unmet need by providing a microfluidic platform for "cells-on-a-chip" applications. Integrated into the platform are interconnect and pulse-free peristaltic pump technology. The platform offers many advantages over conventional approaches today, including, ease-of-use, reliability, flexibility, and accurate flow control. Additionally the platform offers a unique method of environmental control for the culture. Conventionally this is achieved with an incubator. However, for microfluidic applications, incubators are challenging as real-time analyses cannot be performed without disturbing the cultures, and they prevent pumps, microscopes and detectors from being placed adjacent to the cultures, as analytical instrumentation should not be exposed to elevated humidity and temperature.

Typically in cell culture experiments where cells are grown in open or vented containers, incubators are used to control carbon dioxide concentration, temperature, humidity and sometimes oxygen concentration. In contrast to this "open" system, the platform of the present invention is "sealed" in nature. Cell culture media is delivered from a sealed container to the microdevice and then either returned to the media container, or alternatively deposited in a collection vessel. The platform design allows a user easy access to the media container, so that the media can be freshened when desired. The media container is a sealed vessel which can be used for several months at a time, containing volatile, de-gassed solvents. As any slight change in solvent composition from evaporation, or introduction of even small amounts of solubilized gas, would detrimentally affect media quality, these bottle types eliminate gaseous exchange with the external atmosphere. Therefore, in an embodiment cell culture media is contained in this bottle, and the head space filled with the desired $CO_2$ (typically 5-10%) and/or $O_2$ concentration prior to sealing the bottle top. As the tubing used will not allow for gas exchange, the concentration of $CO_2$ and $O_2$ in the system can be maintained by controlling its concentration in the headspace of the media bottle. If pH is found to drift slowly over time, $CO_2$ and/or $O_2$ could be trickled into the bottle headspace to adjust the pH. Preferably, the platform can contain gas mixers, with each microdevice having a dedicated media bottle. Furthermore, since the proposed system is sealed in nature, there is no possibility of evaporation occurring, and thus there is no need to control humidity. Therefore, this approach is able to meet $CO_2$, $O_2$ and humidity requirements for cell growth by a simpler method than a traditional incubator. However, to meet the temperature control requirement, each insert is resistively heated, using conventional technology, to a user defined temperature between about 4°

C. and about 70° C. and preferably about 37° C. The temperature of each insert can be controlled independently. To aid in maintaining temperature stability, a removable cover can be placed over each insert, making a heated chamber. These covers can have gasket-based mouse holes cut to facilitate tubing and/or wires reaching the microdevices, and the covers can be removed for short periods.

The present invention is very flexible and is capable of accommodating a wide variety of microfluidic devices. In addition to the advantages discussed previously, the platform also offers additional benefits. The 96-well plate format of the inserts is a standard footprint, compatible with many microscope stages and other detectors. By supplying extra tubing and wire, the entire insert can be removed from the platform and placed in a nearby detector (such as a microscope stage) for short periods. Allowance of real-time analyses is a remarkable advantage which is simply not possible with the classical incubator approach used today. Additionally the present platform allows for user customization. For example, if backpressure on the system is desired to more closely mimic biological conditions, a flow restrictor could be placed in-line.

Culturing cells in microfluidic devices promises improved in vitro models that are able to more closely mimic in vivo environments than classic cell culture, offering more accurate correlation with in vivo results for toxicology, drug development and biomedical research. To meet this need, herein provided is a flexible, universal platform, capable of interfacing a wide variety of devices with the macro-world, in a user-friendly, robust and reliable manner.

The merging of cell culture and microfluidic technology has resulted in improved in vitro models for toxicity studies, drug development, and biomedical research. The reason why microfluidic approaches provide a more accurate in vitro model of in vivo effects is because devices can be designed with unique properties to closely mimic the in vivo environment. Specifically the micrometer dimensions in the devices allow for a high surface area to volume ratio, leading to more effective nutrient transfer, and allowing a more in vivo-like cellular environment in terms of cell secretion and signaling. Furthermore there is no turbulence in the microchannels as fluid flow is laminar, allowing the only method of mass transport to be through diffusion, similar to a cell's natural environment. Consequently microfluidic approaches allow for biomolecular gradients to be imitated, and additionally microfluidic devices allow for 3D cell culture.

The invention will be further illustrated with reference to the following specific examples. It is understood that these examples are given by way of illustration and are not meant to limit the disclosure or the claims to follow.

Example 1—Comparison of Fluid Delivery

Figure 3A:
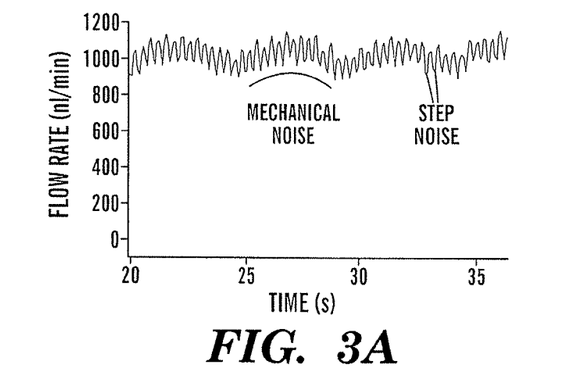
FIG. 3A is a graph of the flow rate vs. time of a conventional syringe pump.
Figure 3B:
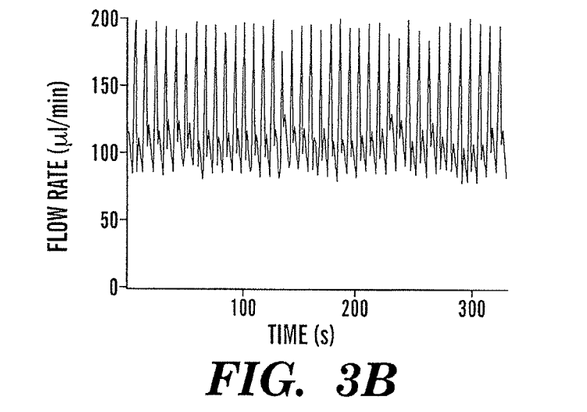
FIG. 3B is a graph of the flow rate vs. time of a conventional peristaltic pump.

Conventional microfluidic systems typically use syringe pumps for fluid delivery, despite the fact that syringe pumps are notorious for inconsistent delivery especially when observed over seconds, milliseconds, and microsecond time frames. The flow at any given time interval or sampling rate must be considered as the performance averaged over time intervals, such as seconds or minutes. This may provide a significantly worse result when measured with faster sampling rates, such as faster than a second. Syringe pump flow rates vary significantly when flow measurements are read at rates in the seconds regime or faster. Error from the desired flow may be from several percent or higher. Manufacturers often base performance numbers resulting from expelling the syringe volume into a gravimetric scale and thus the performance is based on an averaged time. Inaccurate flow delivery that pulses and varies from the desired set point even for short durations will have a negative influence on cell growth by resulting in incorrect shear stress. Syringe pump performance may be improved in a comparative example by adding restriction (increased back pressure) to the system but at a sacrifice in the ability to change flow rate quickly. That is, added restriction will decrease rate of change when moving to a different flow rate set point. From a lead screw design, as the plunger is pushed into the barrel in incremental steps, syringe pumps create a pulsatile flow, as shown in FIG. 3A. The extent of the pulsation is dependent on the size of the syringe used, with larger syringes creating a more pulsating flow than smaller syringes. However, smaller syringes need to be filled more frequently. Additionally, syringe pumps are unable to start and stop flow quickly. An alternative to syringe pumps are peristaltic pumps. These traditional peristaltic pumps also suffer from notorious flow pulsations created by the rollers and the inherent change in the internal diameter of the tubing during the tube compression, as shown in FIG. 3B. Volume measured over longer time frames of seconds to minutes is not indicative of performance at any given faster acquisition, such as sample rates less that 1 second. FIG. 3B displays a sampling rate every 40 milliseconds and demonstrates the flow changing in excess of 50 to 100%. Additionally, flow rates can swing dramatically from minor changes in backpressure and temperature and become more significant when operating in the flow regime of 10 of microliters or less.

Figure 3C:
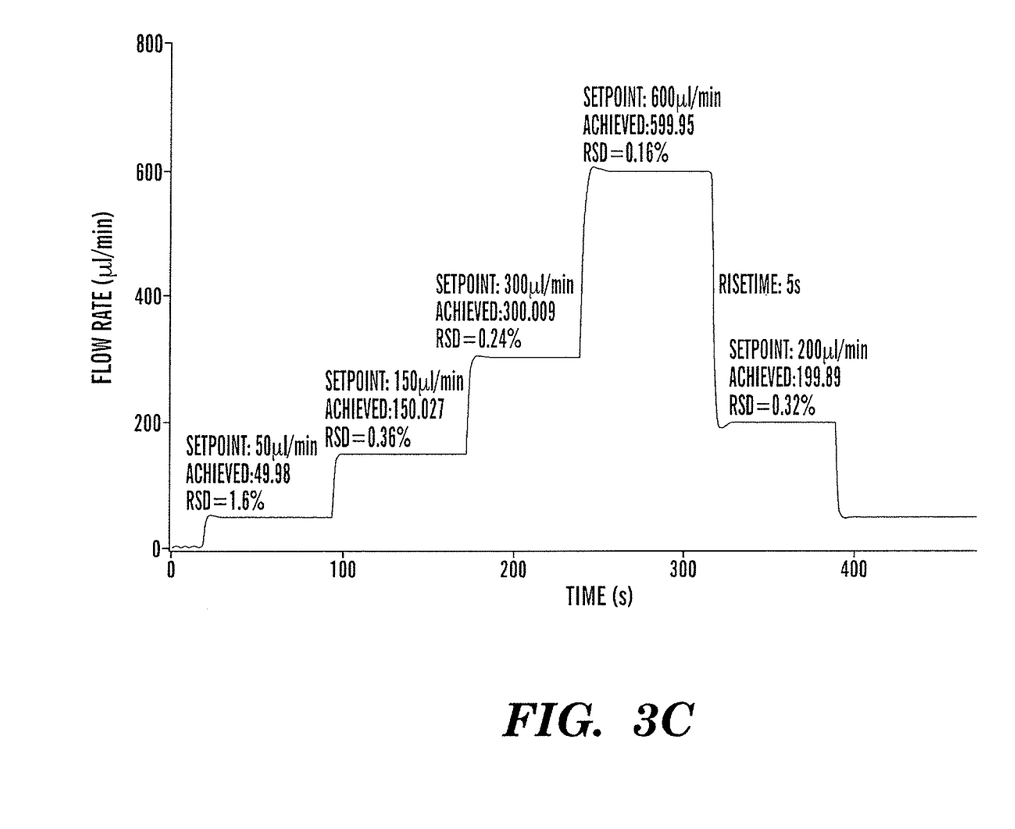
FIG. 3C is a graph of the flow rate vs. time of a peristaltic pump with flow control in accordance with an embodiment of the present invention.

A comparison of fluid delivery from a syringe pump FIG. 3(A) having both mechanical and step noise, a traditional peristaltic pump FIG. 3(B) having significant pulsing from the rollers pinching the tubing, and the fluid delivery system in accordance with the present invention, as represented by the peristaltic pump with continuous flow control feedback FIG. 3(C) was performed in Example 1. In the graph shown in FIG. 3(C) the pump was shown to quickly and accurately achieve and maintain a user defined flow rate with very low relative standard deviation.

With the critical role that flow rate plays on the cell seeding process used to establish a microfluidic culture and on shear stress in maintaining cultures, it would be advantageous to have a highly accurate means of fluidic control. To fill this unmet need, the present invention provides, as shown in this example, peristaltic pump technology, to create a pulse-free fluidic pump with accurate fluid delivery. The peristaltic pump has an integrated flow sensor, which continuously monitors flow rate with feedback, ensuring that the user-defined rate is always being delivered. The pump shown in Example 1 FIG. 3C has an accuracy of ±0.1%, a precision of 0.5% RSD, and is able to operate in both forward and reverse flow modes. To demonstrate performance, the pump was benchmarked against a syringe pump and a conventional peristaltic pump, as shown in FIG. 3. The results of this example clearly indicate that a closed loop feedback integrated with the peristaltic pump mechanism in accordance with the present invention provides more accurate flow control, with the added benefit of being able to start and stop flow quickly, than prior art devices.

Example 2—Effect of Shear Stress

Figure 5:
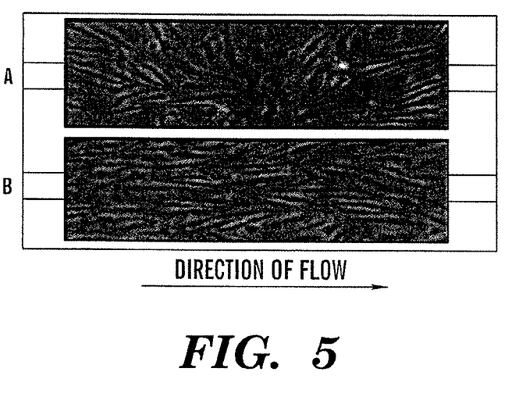
FIG. 5A shows endothelial cells in a static (no flow) and FIG. 5B shows endothelial cells exposed to flow in a parallel-plate flow chamber.

The present example shows the effect of shear stress on the cell growth and morphology of endothelial cells. The experiment was carried out using a parallel-plate flow chamber. FIG. 5A was conducted under static conditions and the cells are not aligning in a discernible pattern. FIG. 5B shows human endothelial cells that were exposed to physiological stress of approximately 6 dynes/cm$^2$ for 12 hours and aligned with the direction of blood flow.

Example 3—Cell Growth

Figure 6:
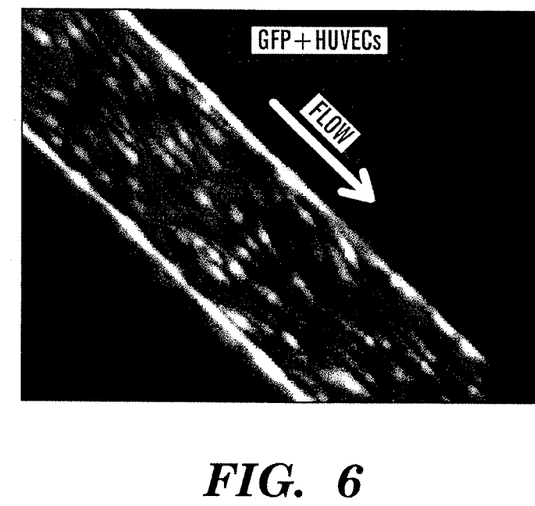
FIG. 6 is a live fluorescence imaging of human endothelial cells grown in accordance with an embodiment of the present invention.

FIG. 6 shows live fluorescence imaging of human endothelial cells in a microvascular network. The culture was run under physiological shear flow of 11 microliters/min. (which provides a shear stress of approximately 17 dyne/cm$^2$) with the closed-loop feedback controlled peristaltic pump of the present invention. Under the physiologic shear stress and flow provided by the present invention, actual cell growth occurs and the endothelial cells align in the direction of flow.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for providing a fluid flow, comprising:
providing a fluid source in a fluidic system;
providing a peristaltic or pneumatic pump apparatus capable of providing at least one of positive and negative displacement of the fluid and configured to indirectly displace the fluid to establish a fluid flow within the system;
providing a flow-through in-line flow sensor configured to directly measure the fluid flow;
providing a feed-back control, comprising a process signal speed faster than about 1 second, in communication with the pump apparatus and the in-line flow sensor, wherein the feed-back control is capable of achieving a fluid flow rate in the range of from about 1 microliters/minute to about 20 milliliters/minute and control the fluid flow in response to the flow sensor measurements;
establishing a desired fluid flow rate through the fluidic system by adjusting the pump apparatus in response to the feed-back control in a manner to maintain the fluid flow at a constant velocity with pulsing less than from about 0.01% to about 20% of the set point for the desired fluid flow rate;
exposing living cells directly in the path of the fluid flow; and
maintaining the desired fluid flow rate to a value suitable to grow and maintain the living cells directly in the path of the fluid flow while preventing exceeding said pulsing by operation of the feed-back control.

2. The method of claim 1, wherein the fluid flow has a shear stress value between about 0.01 dynes/cm$^2$ and about 60 dynes/cm$^2$.

3. The method of claim 1, wherein the fluid comprises growth media.

4. The method of claim 1, wherein establishing a desired fluid flow rate through the fluidic system by adjusting the pump apparatus in response to the feed-back control further comprises generating a system backpressure with the use of a pulse dampener or flow restrictor.

5. The method of claim 1, wherein the fluid flow rate is maintained by changing the fluid velocity at a rate of from about 0.01 to about 10 dynes per millisecond.

6. The method of claim 1, wherein the system comprises conduits having an effective circumference ranging from about 6 microns to about 2 centimeters.

7. The method of claim 1, wherein the fluid flow has flow profile ranging from about 0.2 Hz to about 10 Hz.

8. The method of claim 1, further comprising collecting a sample of the fluid without disrupting the fluid flow rate following the exposing living cells to the fluid flow.

9. The method of claim 1, further comprising adjusting the temperature of the fluid following the providing a fluid source.

10. The method of claim 1, further comprising removing bubbles from the fluid without disrupting the fluid flow rate following the establishing a desired fluid flow rate.

11. The method of claim 1, wherein the system is capable of maintaining the fluid flow rate and keeping the cells alive for longer than about 12 hours.

12. The method of claim 1, further comprising selectively trapping bubbles from the fluid without disrupting the fluid flow rate following the establishing the desired fluid flow rate.

13. The method of claim 1, where the fluid comprises a gas composition having a concentration of at least one of $CO_2$, $O_2$, and N, further comprising controlling the concentration.

14. The method of claim 1, where the fluid pH is buffered.

15. The method of claim 1, wherein the flow sensor is a thermal sensor in contact with an exterior surface of a fluid transporting tube such that the fluid flow avoids direct contact with the sensor.

16. The method of claim 1, wherein the feed-back control is capable of achieving a fluid flow rate of 0.5 microliters/minute.

17. A method for providing a fluid flow, comprising:
providing a fluid source in a fluidic system;
providing a fluid displacement pump apparatus capable of providing at least one of positive and negative displacement of the fluid and configured to indirectly displace the fluid to establish a fluid flow within the system;
providing a flow-through in-line flow sensor configured to directly measure the fluid flow;
providing a feed-back control, comprising a process signal speed faster than about 1 second, in communication with the apparatus and the in-line flow sensor, wherein the feed-back control is configured to achieve a fluid flow rate in the range of from about 1 microliter/minute to about 20 milliliters/minute and control the fluid flow in response to the flow sensor measurements;
establishing a desired fluid flow rate through the fluidic system by adjusting the fluid displacement apparatus in response to the feed-back control in a manner to maintain the fluid flow at a constant velocity with pulsing less than from about 0.01% to about 20% of the set point for the desired fluid flow rate;
exposing living cells directly in the path of the fluid flow; and
maintaining the desired fluid flow rate to a value suitable to grow and maintain the living cells directly in the path of the fluid flow while preventing exceeding said pulsing by operation of the feed-back control.

18. The method of claim 17, wherein the pulsing is maintained at less than about 5% of the set point for the desired fluid flow rate.

19. The method of claim 17, wherein the fluid flow rate set point is in a range of from about 1 microliter/minute to about 1 milliliter/minute.

20. The method of claim 17, wherein the feed-back control is capable of achieving a fluid flow rate of 0.5 microliters/minute.

* * * * *